United States Patent
Garner, III

[11] Patent Number: 6,111,249
[45] Date of Patent: Aug. 29, 2000

[54] SUBMERGIBLE OPTICAL SENSOR HOUSING WITH PROTECTIVE SHUTTER AND METHODS OF OPERATION AND MANUFACTURE

[75] Inventor: William Garner, III, Austin, Tex.

[73] Assignee: Hydrolab Corporation, Austin, Tex.

[21] Appl. No.: 09/118,405

[22] Filed: Jul. 17, 1998

[51] Int. Cl.[7] ............................... H01J 40/14; H01J 5/02
[52] U.S. Cl. ...................... 250/239; 250/573; 250/216; 250/233
[58] Field of Search .................. 250/239, 216, 250/232, 233, 237 R, 573, 574; 356/432, 436

[56] References Cited

U.S. PATENT DOCUMENTS

| | | |
|---|---|---|
| 1,153,945 | 9/1915 | Mustin . |
| 1,178,435 | 4/1916 | Wilson . |
| 2,298,063 | 10/1942 | MacPherson ................................. 88/1 |
| 2,439,087 | 4/1948 | Harvey ........................................ 95/53 |
| 2,745,131 | 5/1956 | Auwärter ................................... 15/255 |
| 3,754,145 | 8/1973 | Leaf ......................................... 250/575 |
| 4,114,308 | 9/1978 | Parker ...................................... 250/239 |
| 4,614,050 | 9/1986 | Stevens .................................... 42/1.01 |
| 4,701,959 | 10/1987 | Asai et al. .................................. 382/1 |
| 5,161,055 | 11/1992 | Blechschmidt .......................... 359/508 |
| 5,605,841 | 2/1997 | Johnsen et al. .......................... 436/164 |

*Primary Examiner*—John R. Lee
*Assistant Examiner*—Glenn T Kinnear
*Attorney, Agent, or Firm*—Baker Botts L.L.P.

[57] ABSTRACT

An apparatus for housing a submergible optical sensor is provided. The apparatus comprises a sensor body having a sensor opening. The sensor body is operable to protect a sensor when submerged in a fluid. A shutter is disposed above the sensor opening. A motor couples to the shutter and can rotate the shutter. A controller couples to the motor and is operable to cause the motor to rotate the shutter such that the sensor opening is exposed when the sensor takes a measurement. The controller is further operable to cause the motor to rotate the shutter such that the shutter covers the sensor opening when the sensor is not taking a measurement.

29 Claims, 1 Drawing Sheet

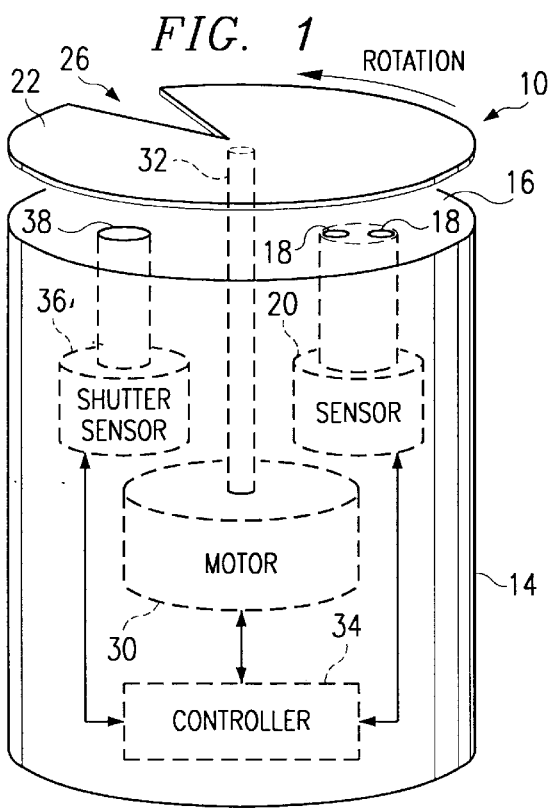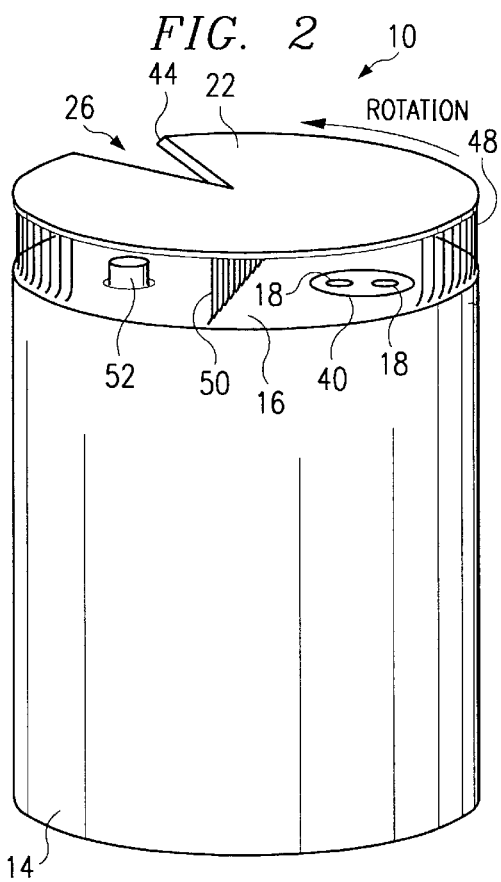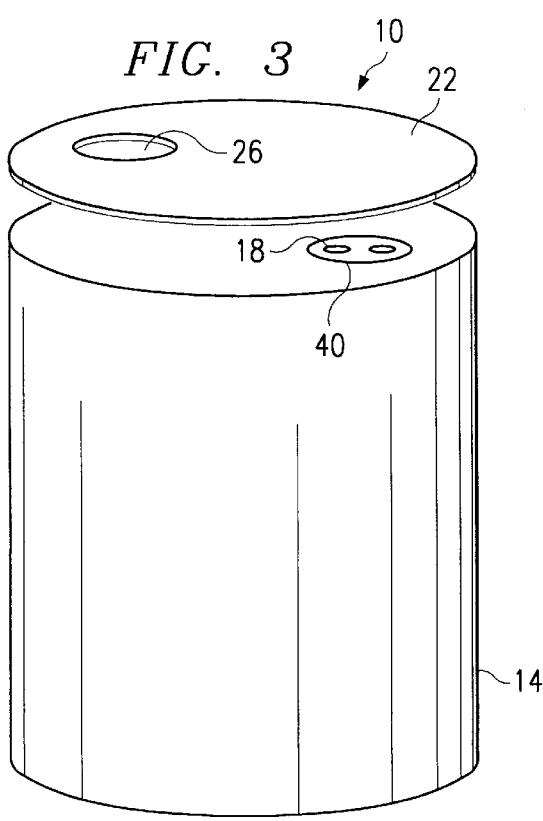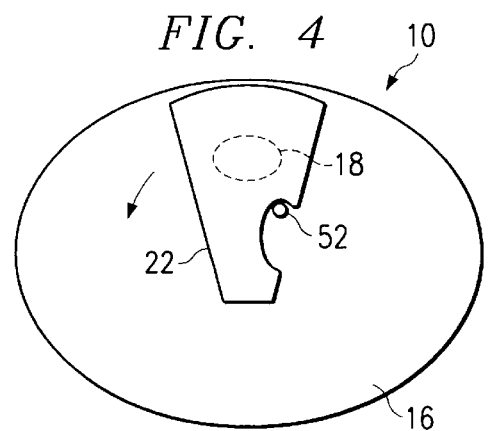

SUBMERGIBLE OPTICAL SENSOR HOUSING WITH PROTECTIVE SHUTTER AND METHODS OF OPERATION AND MANUFACTURE

TECHNICAL FIELD OF THE INVENTION

The present invention relates generally to the field of sensor housings, and more specifically to a submergible optical sensor housing with protective shutter and methods of operation and manufacture.

BACKGROUND OF THE INVENTION

Optical and other sensors can be submerged in fluid to take various measurements. For example, a fluorescent probe type of optical sensor that is submerged in water can measure the concentration of chlorophyl. Such a measurement can give an indication of waterborne plant life.

Submerged optical sensors often exhibit degraded accuracy over time due to fouling. Fouling can occur because the fluid in which the sensor is submerged may carry particles that cloud the optical sensor. For example, the fluid may carry dust, soil and sediment and may deposit these materials over the sensor. Organic material, such as algae, may also grow or form on the sensor, further inhibiting the sensor's ability to take accurate measurements.

Some conventional submergible sensor housing systems attempt to combat these problems by employing a wiping mechanism to clean the area the optical sensor uses to take measurements immediately preceding each measurement. However, such conventional systems are deficient because the wiping mechanism does not operate sufficiently to prevent fouling of the optical surface between measurements. Further, the wiping mechanism itself may become fouled by supporting organic life or deteriorating in the submerged conditions.

SUMMARY OF THE INVENTION

In accordance with the present invention, a submergible optical sensor housing with protective shutter and methods of operation and manufacture are disclosed that provide significant advantages over prior developed sensor housings.

According to one aspect of the present invention, the submergible optical sensor housing includes a sensor body for housing an optical sensor. The sensor body can protect the sensor from a fluid in which the sensor body is submerged. The sensor body has a sensor opening formed in an exterior surface proximate the optical sensor. A shutter is disposed above the sensor opening. A motor is coupled to the shutter and is operable to rotate the shutter with respect to the sensor body. A controller is coupled to the motor and is operable to cause the motor to rotate the shutter such that the sensor opening is exposed when the sensor takes a measurement. The controller is further operable to cause the motor to rotate the shutter such that the shutter covers the sensor opening when the sensor is not taking a measurement.

In one embodiment, the submergible optical sensor housing also includes a shutter position sensor coupled to the controller where the shutter position sensor can determine the placement of the aperture of the shutter with respect to the sensor opening.

In another embodiment, the submergible optical sensor housing further includes a layer of antifouling material applied to a bottom surface of the shutter.

It is a technical advantage of the present invention that the deposition of materials on the sensor opening is reduced by physically covering the sensor opening except when the sensor opening is in use.

It is another technical advantage that the shutter prevents photosynthetic growth in the sensor opening by darkening the sensor opening when the sensor is not in use.

It is a further technical advantage of the present invention that the rotation of the shutter can move sediment or other fouling away from the sensor opening by agitating the fluid around the sensor opening.

It is an additional technical advantage of the present invention that biofouling can be reduced near the sensor opening.

Other technical advantages should be apparent to one of ordinary skill in the art in view of the specification, claims, and drawings.

BRIEF DESCRIPTION OF THE DRAWINGS

A more complete understanding of the present invention and advantages thereof may be acquired by referring to the following description taken in conjunction with the accompanying drawings, in which like reference numbers indicate like features, and wherein:

FIG. 1 is a schematic diagram of one embodiment of a submergible optical sensor housing with protective shutter according to the present invention;

FIG. 2 is a schematic diagram of a second embodiment of a submergible optical sensor housing with protective shutter according to the present invention;

FIG. 3 is a schematic diagram of another embodiment of a submergible optical sensor housing with protective shutter according to the present invention; and FIG. 4 is a top view of a further embodiment of a protective shutter for a submerged optical sensor housing according to the present invention.

DETAILED DESCRIPTION OF THE INVENTION

FIG. 1 is a schematic diagram of one embodiment of a submergible optical sensor housing with protective shutter according to the present invention. The sensor housing, indicated generally at 10, includes a sensor body 14. Sensor openings 18 are formed into an exterior surface of sensor body 14. For example, sensor openings 18 could comprise an transparent material such as glass formed into openings in the exterior surface of sensor body 14. The embodiment shown in FIG. 1 includes two sensor openings 18. However, it should be understood that fewer or more sensor openings 18 may be formed into sensor body 14. Further, in the embodiment shown, sensor openings 18 are formed into an end exterior surface 16. The invention contemplates that sensor openings 18 also may be formed in other surfaces of sensor body 14. As shown in FIG. 1, an optical sensor 20 can be housed inside sensor body 14 and situated proximate to sensor openings 18. Optical sensor 20 can be any suitable sensor operable to take measurements in a submerged situation. Optical sensor 20 can function, for example, by making optical measurements of the environment through sensor openings 18.

A shutter 22, which includes an aperture 26, is disposed above sensor openings 18. Shutter 22 is coupled to a motor 30, wherein motor 30 is operable to rotate shutter 22 with respect to sensor body 14. It should be understood that numerous devices are available that could perform the function of motor 30. For example, the company MICRO MO sells several motor types sufficient to perform as motor 30. Further, motor 30 can be a DC motor or other type of motor. For example, motor 30 could comprise a stepper-type motor which rotates a predetermined number of degrees. In the embodiment of FIG. 1, shutter 22 is coupled to motor 30 via shaft 32. However, other conventional methods of attachment can be used. Motor 30, in turn, is coupled to controller 34. Controller 34 is operable to signal motor 30 to rotate shutter 22. For example, controller 34 could comprise a processor, memory, and associated circuitry. In an alternate embodiment, controller 34 could comprise a more simple structure operable to apply current to a DC motor 30.

The embodiment of FIG. 1 further includes a shutter position sensor 36 coupled to controller 34. Shutter position sensor 36 is proximate to a shutter position sensor opening 38 and can sense a rotation of shutter 22. For example, shutter position sensor 36 could comprise a light sensing and a light propagating device. A reflective piece could be placed on the underside of shutter 22 such that when aperture 26 was proximate sensor openings 18, the reflective piece can be proximate shutter position sensor opening 38. Accordingly, shutter position sensor 36 could detect the reflected light through shutter position sensor opening 38 when aperture 26 was proximate sensor openings 18. In an alternate embodiment, shutter sensor 36 could comprise a detector operable to detect a magnetic field. A magnet could be coupled to shutter 22 such that shutter sensor 36 could detect the position of aperture 26 with respect to sensor openings 18.

In operation, sensor housing 10 is submerged in a fluid. For example, an operator may wish to make measurements of the algae growth in a lake. Optical sensor 20 can take optical measurements of the water through sensor openings 18 when shutter 22 is stopped, or "parked", such that aperture 26 exposes sensor openings 18. Controller 34 can cause motor 30 to rotate shutter 22 such that aperture 26 exposes sensor openings 18 only when sensor 20 takes measurements. When measurements are not being taken, controller 34 can park shutter 22 such that aperture is away from sensor openings 18. Shutter sensor 36 can signal controller 34 and provide data as to the position of aperture 26 by taking measurements through shutter sensor opening 38. Further, in operation, controller 34 can be programmed to signal motor 30 to rotate shutter 22 with sufficient speed to perturb the fluid in order to remove debris from sensor openings 18. Further, controller 34 can be programmed to initiate rotation of shutter 22 periodically in addition to rotation when sensor measurements are made.

It is a technical advantage that shutter 22 can protect the end surface 16 of sensor body 14 as well as sensor openings 18 from fouling that can occur in underwater environments. It is another technical advantage that periodic rotation of shutter 22 can minimize the growth of organic or mineral substrates between uses of optical sensor 20. A further technical advantage is that the sensor housing 10 can prevent photosynthetic growth in the area of sensor openings 18 because shutter 22 darkens sensor openings 18 when measurements are not being taken.

FIG. 2 is a schematic diagram of a second embodiment of a submergible optical sensor housing with protective shutter according to the present invention. As shown, the sensor housing, indicated generally at 10, is similar to sensor housing 10 of FIG. 1. Sensor body 14 includes sensor openings 18 formed into an end exterior surface 16. A shutter 22 is disposed above sensor openings 18 and includes aperture 26. Shutter 22 further includes a sloped edge 44. Sensor housing 10 can further include biocidal agents disposed on area 40 proximate to sensor openings 18.

It should be understood that numerous biocidal agents could be used to prevent organic growth. The embodiment of FIG. 2 further comprises a skirt 48 of material coupled around the perimeter of shutter 22. FIG. 2 only shows a portion of skirt 48, but the present invention contemplates that skirt 48 could surround the entire perimeter of shutter 22. Further, a brush 50 can be coupled to the underside of shutter 22 and can wipe sensor opening 18 when shutter 22 rotates.

In operation, sensor housing 10 of FIG. 2 is similar to that of FIG. 1. However, the addition of a biocidal agent in area 40 can minimize the growth of organic contaminants in area 40 proximate to sensor openings 18. Further, skirt 48 further can prevent contaminants from entering under shutter 22 to contaminate sensor openings 18. When the sensor takes measurements, shutter 22 is rotated until sensor openings 18 are exposed. After a measurement is taken, shutter 22 can rotate in the opposite direction until aperture 26 is no longer above sensor openings 18.

Referring back to FIG. 2, brush 50 can wipe contaminants from sensor openings 18 as shutter 22 rotates. Also, sloped edge 44 of shutter 22 operates to further perturb water as shutter 22 rotates, which can clear contaminants from sensor openings 18. As discussed, when measurements are not being taken through sensor openings 18, shutter 22 can be parked such that aperture 26 is away from sensor opening 18. As discussed, this can retard photosynthetic growth around sensor opening 18. A further embodiment of the present invention can employ the use of an anti-fouling coating applied to a bottom surface of shutter 22. Such a coating can further reduce the risk of contamination.

An additional embodiment of the present invention could combine features of the embodiments shown in FIGS. 1 and 2. For example, one embodiment could comprise a motor 30 operable to rotate shutter 22 at variable speeds. Further, the shutter could include an edge 44 of the aperture 26 that is sloped. In operation, motor 30 could rotate shutter 22 at high speeds. Such high speed rotation could perturb the fluid in order to remove contaminants. Sloped edge 44 could further allow the fluid to propel contaminants away from sensor openings 18. Alternatively, such an embodiment could comprise a motor 30 operable to rotate shutter 22 clockwise and counterclockwise with respect to sensor body 14. Motor 30 could alternate the direction of rotation in order to further agitate the fluid and remove contaminants.

FIG. 3 is a schematic diagram of another embodiment of a submerged optical sensor housing with protective shutter according to the present invention. Sensor housing 10 includes a sensor body 14 with sensor openings 18 formed into an exterior surface. Shutter 22, which includes aperture 26, is disposed above sensor openings 18. In the embodiment of FIG. 3, aperture 26 is formed as a circular hole formed in shutter 22. In operation, sensor housing 10 performs a similar function as to that of FIGS. 1 and 2. However, as FIG. 3 shows, the current invention contemplates an aperture 26 having various shapes.

Further in the embodiment of FIGS. 1, 2, and 3 shutter 22 is disposed above an end surface 16 of sensor body 14 but not in contact with top surface 16. However, it is contemplated that shutter 22 could be in contact with top surface 16 when not in motion. In operation, such an embodiment could raise shutter 22 slightly above top surface 16, and then rotate shutter 22.

FIG. 4 is a top view of a further embodiment of a protective shutter for a submerged optical sensor housing according to the present invention. In this embodiment, shutter 22 is disposed above top surface 16 of sensor housing. As shown, shutter 22 covers sensor opening 18 and rests against stop pin 52.

In operation, when a measurement is to be taken, a motor rotates shutter 22 counterclockwise as shown. Shutter 22 is formed such that it will contact stop pin 52 and stop rotating such that sensor opening 18 is exposed. A measurement can then be taken. After the measurement, shutter 22 will rotate clockwise and again cover sensor opening 18.

Although the present invention has been described in detail, it should be understood that various changes, substitutions and alterations can be made thereto without departing from the spirit and scope of the invention as defined by the appended claims.

What is claimed is:

1. An apparatus for housing a submergible optical sensor, the apparatus comprising:
   a sensor body for housing a sensor, the sensor body having a sensor opening formed in an exterior surface proximate the sensor, wherein the sensor body is operable to protect the sensor when submerged in a fluid;
   a shutter disposed external to the sensor body and above the sensor opening;
   a motor coupled to the shutter and operable to rotate the shutter with respect to the sensor body; and
   a controller coupled to the motor, the controller operable to cause the motor to rotate the shutter such that the sensor opening is exposed when the sensor takes a measurement, the controller further operable to cause the motor to rotate the shutter such that the shutter covers the sensor opening when the sensor is not taking a measurement.

2. The apparatus of claim 1, further comprising a shutter position sensor coupled to the controller, the shutter position sensor operable to determine the placement of the shutter with respect to the sensor opening.

3. The apparatus of claim 1, wherein the shutter is formed to have an aperture.

4. The apparatus of claim 3, wherein the aperture is pie shaped.

5. The apparatus of claim 3, wherein the aperture is shaped as a circular hole.

6. The apparatus of claim 1, wherein the motor is a DC motor.

7. The apparatus of claim 1, further comprising a skirt of material coupled to a perimeter of the shutter.

8. The apparatus of claim 1, further comprising an antifouling coating applied to a bottom surface of the shutter.

9. The apparatus of claim 1, wherein the motor is operable to rotate the shutter at variable speeds.

10. The apparatus of claim 1, wherein the motor is a stepper-type motor.

11. The apparatus of claim 3, wherein an edge of the aperture is sloped.

12. The apparatus of claim 1, further comprising a biocidal agent disposed proximate the sensor opening.

13. The apparatus of claim 1, further comprising a brush coupled to a lower surface of the shutter, the brush operable to wipe the sensor opening when the shutter rotates with respect to the sensor body.

14. The apparatus of claim 1, wherein the motor is operable to rotate the shutter clockwise and counterclockwise with respect to the sensor body.

15. An apparatus for housing a submergible optical sensor, the apparatus comprising:
   a sensor body for housing a sensor, the sensor body having a sensor opening formed in an exterior surface proximate the sensor, wherein the sensor body is operable to protect the sensor when submerged in a fluid;
   a shutter having an aperture, wherein the shutter is disposed external to the sensor body and above the sensor opening;
   a DC motor coupled to the shutter and operable to rotate the shutter with respect to the sensor body; and
   a controller coupled to the motor, the controller operable to cause the motor to rotate the shutter such that the aperture is proximate the sensor opening when the sensor takes a measurement, the controller further operable to cause the motor to rotate the shutter such that the shutter covers the sensor opening when the sensor is not taking a measurement.

16. The apparatus of claim 15, further comprising a shutter position sensor coupled to the controller, the shutter position sensor operable to determine the placement of the shutter with respect to the sensor opening.

17. The apparatus of claim 15, wherein the aperture is pie shaped.

18. The apparatus of claim 15, wherein the aperture is shaped as a circular hole.

19. The apparatus of claim 15, further comprising a skirt of material coupled to a perimeter of the shutter.

20. The apparatus of claim 15, further comprising an antifouling coating applied to a bottom surface of the shutter.

21. The apparatus of claim 15, wherein the motor is operable to rotate the shutter at variable speeds.

22. The apparatus of claim 15, wherein the motor is a stepper-type motor.

23. The apparatus of claim 15, wherein an edge of the aperture is sloped.

24. The apparatus of claim 15, further comprising a biocidal agent disposed proximate the sensor opening.

25. The apparatus of claim 15, further comprising a brush coupled to a lower surface of the shutter, the brush operable to wipe the sensor opening when the shutter rotates with respect to the sensor body.

26. The apparatus of claim 15, wherein the motor is operable to rotate the shutter clockwise and counterclockwise with respect to the sensor body.

27. A method of operation for a submergible optical sensor, comprising:
   providing a sensor housed and protected by a sensor body, the sensor body operable to protect the sensor when submerged in a fluid, and the sensor body having a sensor opening formed in an exterior surface proximate the sensor;
   rotating a shutter disposed external to the sensor body and above the sensor opening, such that the sensor opening is exposed when the sensor takes a measurement; and
   rotating the shutter such that the shutter covers the sensor opening when the sensor is not taking a measurement.

28. The method of claim 27, further comprising periodically rotating the shutter to remove contaminants.

29. The method of claim 27, further comprising wiping the sensor opening with brush coupled to a lower surface of the shutter, the brush operable to wipe the sensor opening when the shutter rotates with respect to the sensor body.

* * * * *